(12) United States Patent
Townley (10) Patent No.: US 6,695,884 B1
(45) Date of Patent: Feb. 24, 2004

(54) JOINT IMPLANT HAVING POROUS COATING FOR MITIGATION OF WEAR DEBRIS DISPERSION WHEN IMPLANTED

(75) Inventor: Charles O. Townley, Port Huron, MI (US)

(73) Assignee: BioPro, Inc., Port Huron, MI (US)

( * ) Notice: Subject to any disclaimer, the term of this patent is extended or adjusted under 35 U.S.C. 154(b) by 172 days.

(21) Appl. No.: 09/408,409

(22) Filed: Sep. 29, 1999

(51) Int. Cl.$^7$ .................................................. A61F 2/36
(52) U.S. Cl. ................. 623/23.26; 623/23.29; 623/23.36; 623/23.39
(58) Field of Search ................... 623/23.11, 23.12, 623/23.15, 23.2, 23.21, 23.22, 23.23, 23.26, 23.29, 23.3, 23.36, 23.37, 22.4, 22.13, 18.11

(56) References Cited

U.S. PATENT DOCUMENTS

| | | | | |
|---|---|---|---|---|
| 3,683,421 A | * | 8/1972 | Martinie | 623/22.13 |
| 4,406,023 A | * | 9/1983 | Harris | 623/23.11 |
| 4,530,114 A | * | 7/1985 | Tepic | 623/23.36 |
| 4,822,368 A | * | 4/1989 | Collier | 623/22.13 |
| 5,263,988 A | * | 11/1993 | Huebner | 623/22.13 |
| 5,370,698 A | * | 12/1994 | Heimke et al. | 623/18.11 |
| 5,702,448 A | * | 12/1997 | Buechel et al. | 623/18.11 |
| 5,702,483 A | * | 12/1997 | Kwong | 623/22.4 |
| 6,008,432 A | * | 12/1999 | Taylor | 623/23.36 |

OTHER PUBLICATIONS

BioPro, Inc., "Physiological Stress Loading, PSL, Total Hip Replacement System," 1991.
Jacobs, *Soc. Biomaterials Trans.*, Apr. 1998, p.XLVII.
Goodman, *Soc. Biomaterials Trans.*, Apr. 1998, p. XLVIII.
Ramamurti et al., *Soc. Biomaterials. Trans.*, Apr. 1998, p. 5.
Goodman et al., *Soc. Biomaterials Trans.*, Apr. 1998, p.58.
Clineff et al., *Soc. Biomaterials Trans.*, Apr. 1998, p.445.
Amstutz et al., *Soc. Biomaterials Trans.*, Apr. 1998, p.447.
Townley, *Ceramic Trans.*, vol. 48, pp. 23–45, 1995.
ASTM F 75–92, 1992.
ASTM F 799–95, 1995.
ASTM F 1377–98, 1998.
ASTM F 1537–94, 1994.
Ward et al., *Sem. in Arthroplasty*, vol. 10, pp. 124–132, Jul. 1999.

* cited by examiner

*Primary Examiner*—Pedro Philogene
(74) *Attorney, Agent, or Firm*—Christopher John Rudy (57) ABSTRACT

Prosthetic joint replacement ensemble includes an artificial joint implant component having a non-bone-interfacing rough surface for ingrowth of fibrous tissue, preferably about a peripheral boundary. The component can be made of metal, and have the rough surface provided by porous metal coating. When the prosthesis is implanted, the extramedullary rough surface engenders ingrowth of soft fibrous tissue so that it forms, as it were, a reconstituted capsular "bag" in which wear debris from the joint, for example, ultra high molecular weight polyethylene wear debris, is trapped, thus keeping those particles from gaining access to supporting bone at the bone-prosthetic interface. And so, with mitigation of wear debris dispersion, debris wear-induced osteolysis can be ameliorated.

20 Claims, 9 Drawing Sheets

JOINT IMPLANT HAVING POROUS COATING FOR MITIGATION OF WEAR DEBRIS DISPERSION WHEN IMPLANTED

BACKGROUND TO THE INVENTION

I. Field of the Invention

The present invention concerns a prosthetic joint implant having a tissue-integratable rough surface and as a special example a porous coating on a surface other than that which may be commonly provided for the intramedullary prosthetic-bone interface. The invention is for mitigation of latent wear debris dispersion following implantation.

II. Problems and Known Art

Artificial joint implants are known articles of manufacture, which can provide for remarkable remediation of painful and dysfunctional joints. In the known conventional practice of total joint replacement, the concave surface of an ultra high molecular weight polyethylene (UHMWPE) implant mates and articulates with the convex surface of a hard metallic or ceramic component. For example, in an enarthrodial joint such as the hip, a femoral component having a metal or ceramic ball is articulated in match with an UHMWPE acetabular cup.

The femoral component of a total conventional hip replacement generally has a metal stem which is inserted into and stabilizes the composite component within the medullary canal of the proximal femoral shaft, and the preferred total conventional hip replacement femoral component further has a collar at the upper end of the stem which rests upon the resected bone plane of the upper femur. Such component can be one adapted to be stabilized with a surgical cement such as polymethylmethacrylate where there typically is a more smooth but sometimes grooved stem surface for stem integration between it and the intramedullary bone (periprosthetic bone) and/or stabilized by ingrowth of bone from the implant-bone interface, in which case a porous coating is known to cover that part of the stem to be in contact with the periprosthetic bone. See, e.g., BioPro, Inc., "PSL Total Hip Replacement System," 1991. Although they are adapted for particular bodily joints, many other body joint implants are broadly analogous to the hip in such considerations.

Although UHMWPE has been proven to be exceptionally durable, this material is, nonetheless, vulnerable to an unfavorably high rate of wear that certain researchers and practitioners note results in periprosthetic bone dissolution and premature failure of the procedure, which may be seen more disastrously in the hip. For the most common total joint coupling in current use, i.e., cobalt-chrome alloy on UHMWPE, the polyethylene wear rate is typically on the order of 0.1 to 0.3 mm annually, which results in the proliferation of billions of wear particles per year. Over the subsequent years, the massive over-loaded accumulation of particulate wear debris, including a substantial portion of submicron sized particles, gains access to the bone-prosthetic interface and induces an adverse foreign body reaction associated with phagocytic activity and the attendant release of bone-resorptive chemical mediators (periprosthetic osteolysis). Structural bone loss due to debris-induced periprosthetic osteolysis is now commonly cited as a major etiological factor in implant loosening and failure of joint replacement procedures. See, e.g., Jacobs, *Soc. Biomaterials Trans.*, April 1998, p. XLVII. See also, Goodman, Id., p. XLVIII; Ramamurti et al., Id., p. 5; Goodman et al., Id., p. 58; Clineff et al., Id., p. 445; Amstutz et al., Id., p. 447. But see, Townley, *Ceramic Trans.*, Vol. 48, pp. 23–34, 1995 (structure of implant to physiologically stress loading remaining bone stock may play part in ameliorating or precluding initial loosening to hinder or preclude osteolysis).

It would be desirable to ameliorate if not overcome such a problem. It would be desirable to fulfill such a longstanding lack and long felt need in the art.

SUMMARY OF THE INVENTION

The invention provides a prosthetic component comprising an artificial joint implant component having an extramedullary, non-bone-interfacing, soft fibrous tissue-integratable rough surface. One or more components may make up a prosthesis.

The invention is useful in arthroplasty.

Significantly, when the prosthesis is implanted, the exposed out of bone rough surface has been shown to routinely engender ingrowth of soft fibrous tissue so that it forms, as it were, a capsular "bag" in which wear debris from the joint is trapped, thus keeping those particles from gaining access to the bone-prosthetic interface. And so, with mitigation of wear debris dispersion to the periprosthetic bone, the problem in the art of debris wear-induced osteolysis can be ameliorated, if not overcome, and the longstanding lack and long felt need in the art are addressed if not overcome and fulfilled.

BRIEF DESCRIPTION OF DRAWINGS OF THE INVENTION

The drawings form part of the specification hereof. With respect to the drawings, which are not necessarily drawn to scale, the following is briefly noted.

ILLUSTRATIVE DETAIL OF THE INVENTION

The invention can be further understood by the present detail, which may be read in view of the drawings. The same is to be taken in an illustrative and not necessarily limiting sense.

Figures 1, 2, 3:
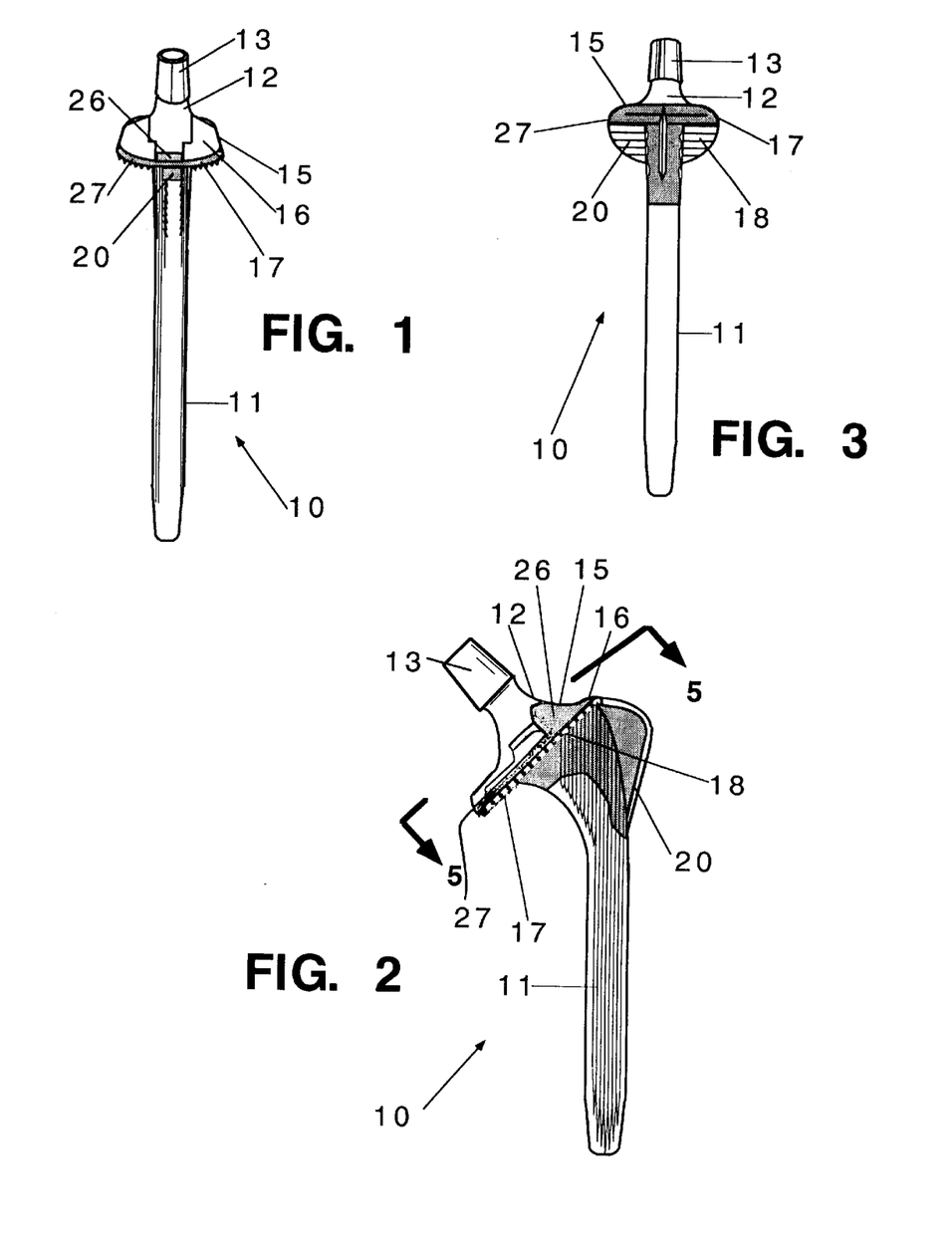
FIG. 1 is a medial view of the invention, embodied as the stem part of a modular femoral component of a physiologically stress loaded total conventional hip joint replacement.
FIG. 2 is a dorsal view of the implant component of FIG. 1.
FIG. 3 is a lateral view of the component of FIGS. 1 & 2.
Figures 4, 5:
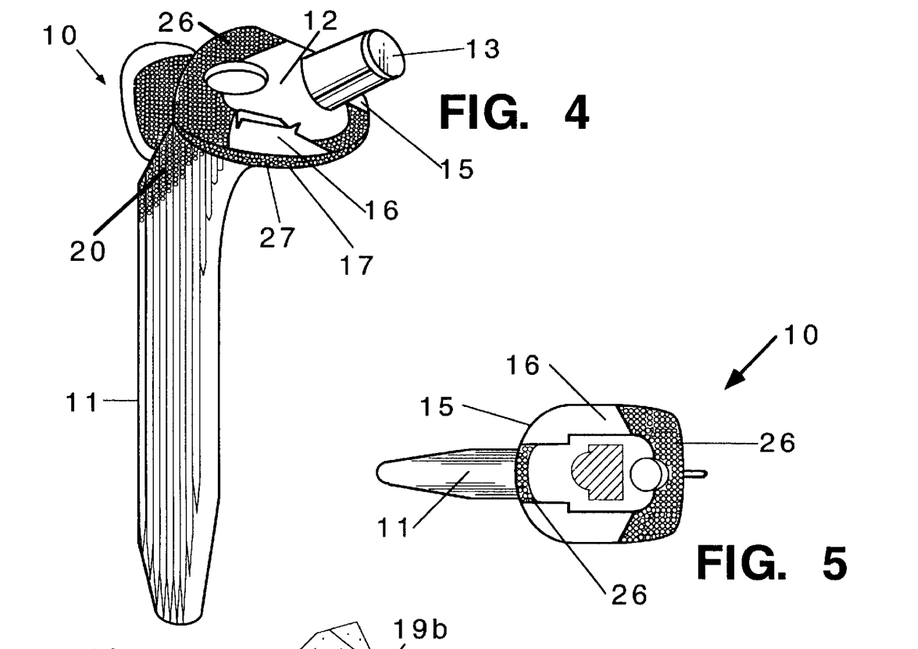
FIG. 4 is a perspective view, taken mainly along the proximal and ventral directions, of the implant component of FIGS. 1–3.
FIG. 5 is a proximal view of the component of FIGS. 1–4, taken in section along 5—5 from FIG. 2.
Figure 6:
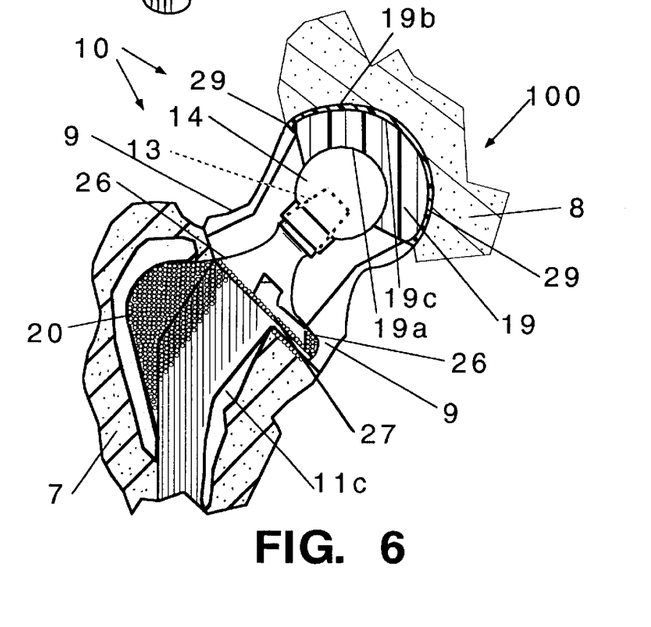
FIG. 6 is a ventral view of the invention, embodied as a conventional total hip replacement joint implant, which includes the implant component of FIGS. 1–5, and a metal-backed acetabular cup having an encircling border of extramedullary porous coating, implanted in the human body, with bones and bag-forming fibrous, capsular-like tissue in section.
Figure 7:
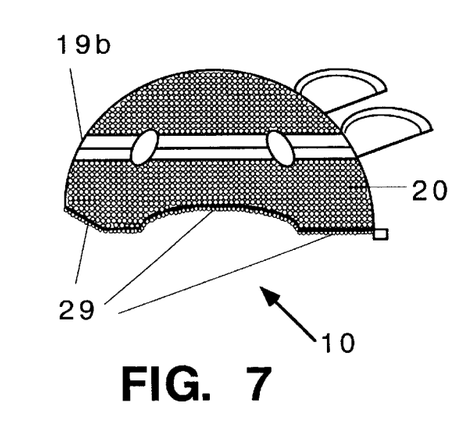
FIG. 7 is a side view of the invention, embodied as a metal backing for an UHMWPE acetabular cup insert such as in FIG. 6.
Figure 8:
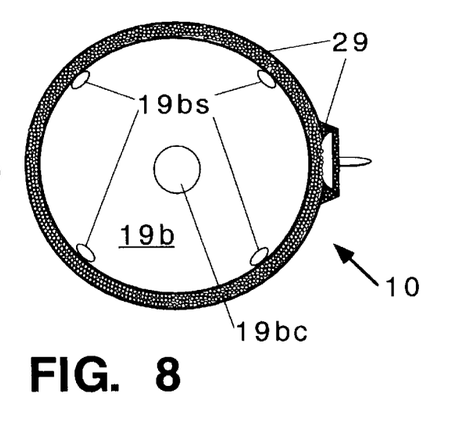
FIG. 8 is a bottom view of the backing of FIG. 7.
Figure 9:
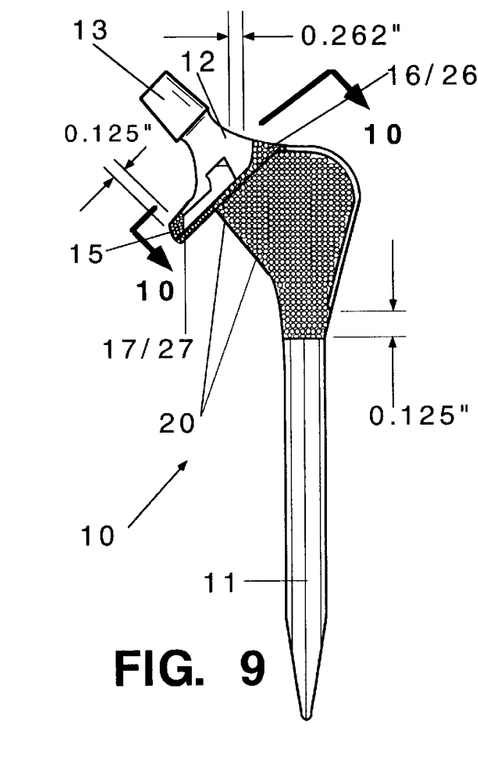
FIG. 9 is a dorsal view of the invention, embodied as a modular conical platform supported femoral hip stem component for total conventional hip joint replacement. Viewed from the reader's perspective, the left hand side of the component is its medial side, and the right hand side of the component is its lateral side.
Figure 10:
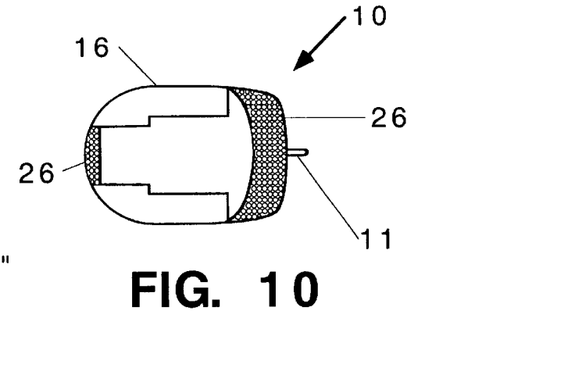
FIG. 10 is a proximal view of the component of FIG. 9, taken in section along 10—10.
Figure 11:
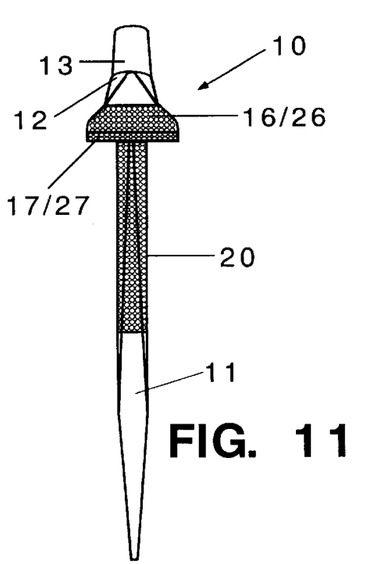
FIG. 11 is a lateral view of the invention, embodied as a stem part of a modular femoral component of a proximal collar loaded, total conventional hip joint replacement, which also has standard porous coating for bone ingrowth fixation.
Figure 12:
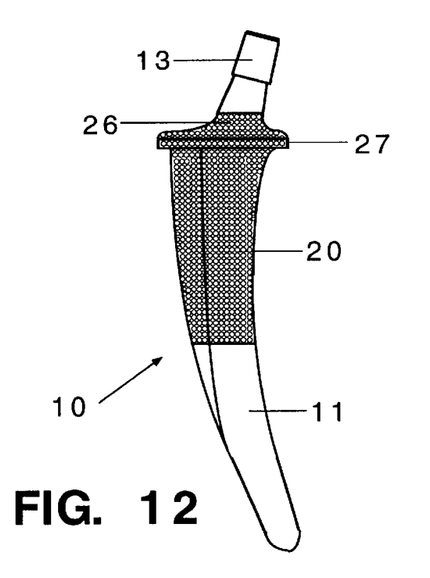
FIG. 12 is a ventral view of the component of FIG. 11, with the dorsal view being a mirror image thereof.
Figure 13:
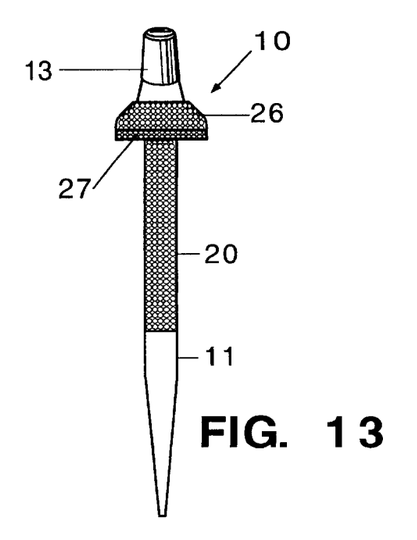
FIG. 13 is a medial view of the component of FIGS. 11 & 12.
Figure 14:
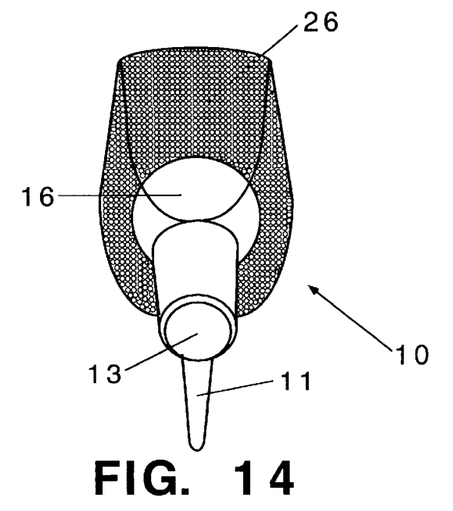
FIG. 14 is a proximal view of the component of FIGS. 11–13.
Figure 15:
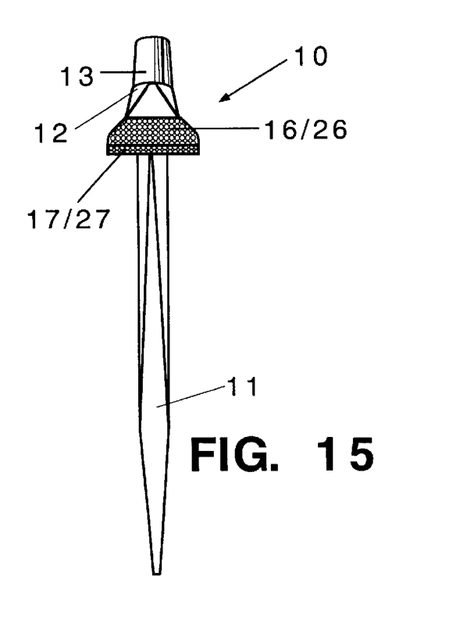
FIG. 15 is a lateral view of the invention, embodied as a stem part of a modular femoral component of a proximal collar loaded, total conventional hip joint replacement, which is intended for cement fixation.
Figure 16:
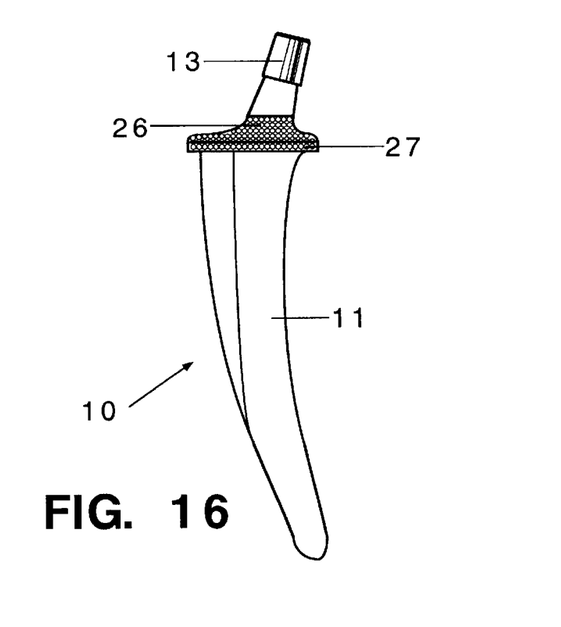
FIG. 16 is a ventral view of the component of FIG. 15, with the dorsal view being a mirror image thereof.
Figure 17:
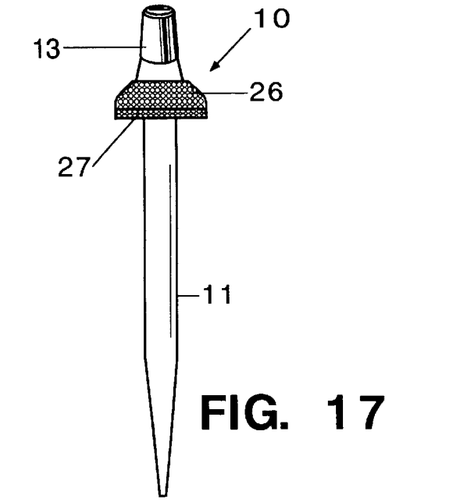
FIG. 17 is a medial view of the component of FIGS. 15 & 16.
Figure 18:
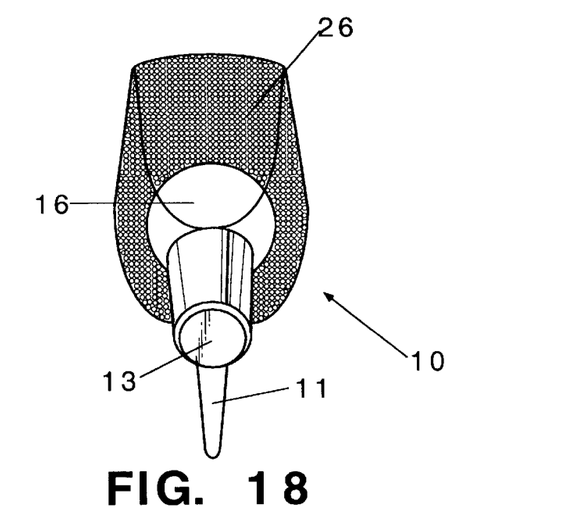
FIG. 18 is a proximal view of the component of FIGS. 15–17.
Figure 19:
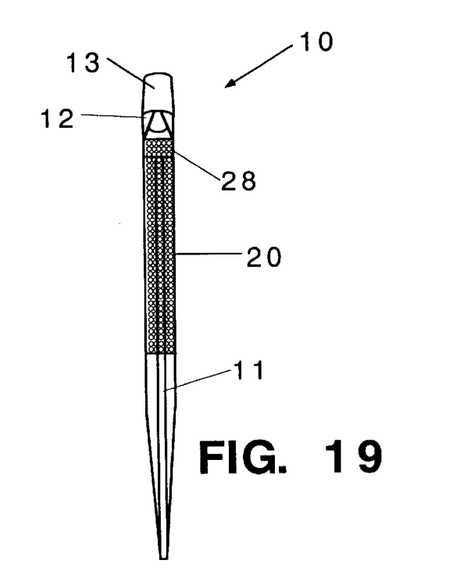
FIG. 19 is a lateral view of the invention, embodied as a stem part of a modular femoral component of a collarless total conventional hip joint replacement, which also has standard porous coating for bone ingrowth fixation of the stem.
Figure 20:
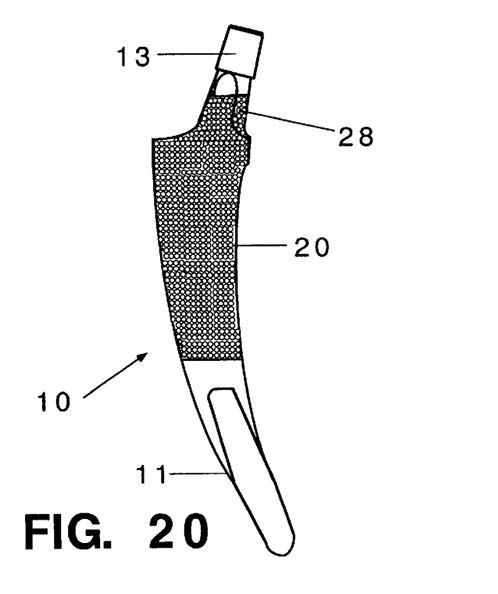
FIG. 20 is a ventral view of the component of FIG. 19, with the dorsal view being a mirror image thereof.
Figure 21:
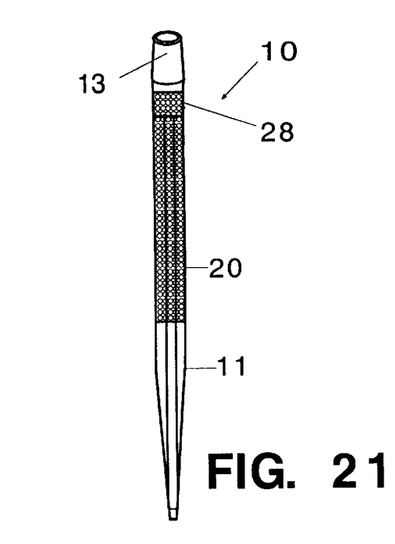
FIG. 21 is a medial view of the component of FIGS. 19 & 20.
Figure 22:
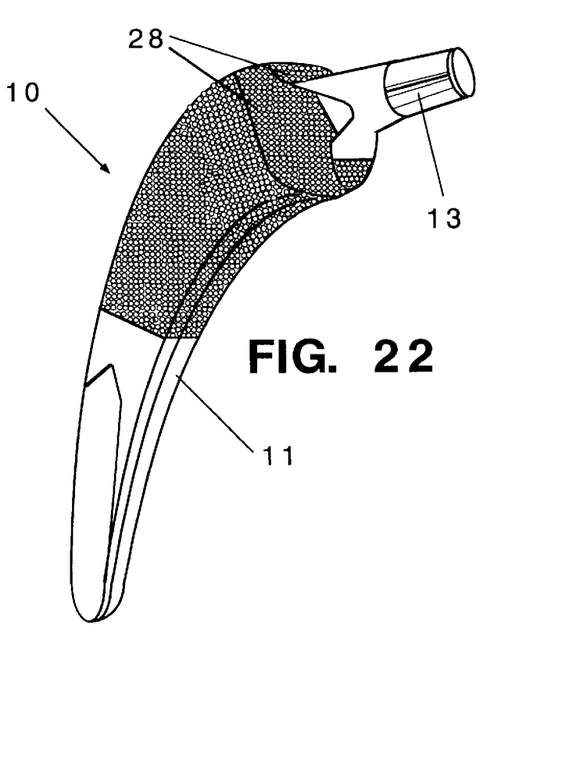
FIG. 22 is a perspective view of the FIGS. 19–21 component.
Figure 23:
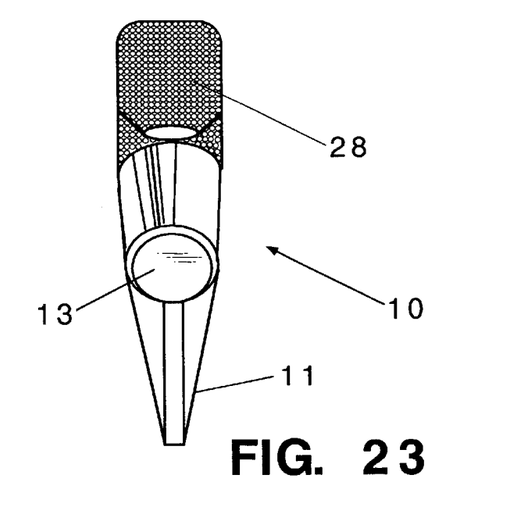
FIG. 23 is a proximal view of the component of FIGS. 19–22.
Figure 24:
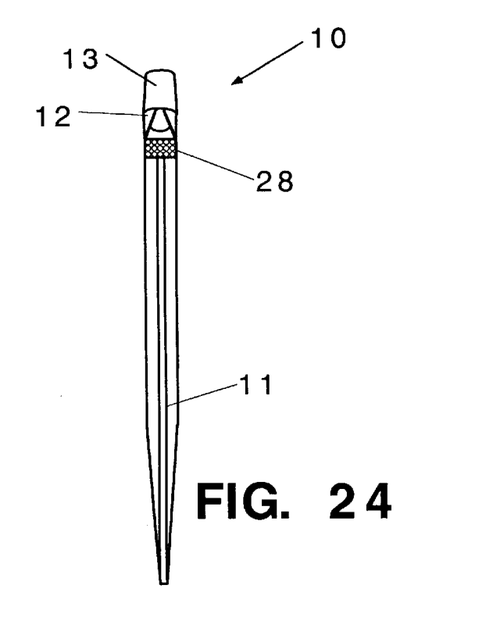
FIG. 24 is a lateral view of the invention, embodied as a stem part of a modular femoral component of a collarless total conventional hip joint replacement, which is also intended for cement fixation.
Figure 25:
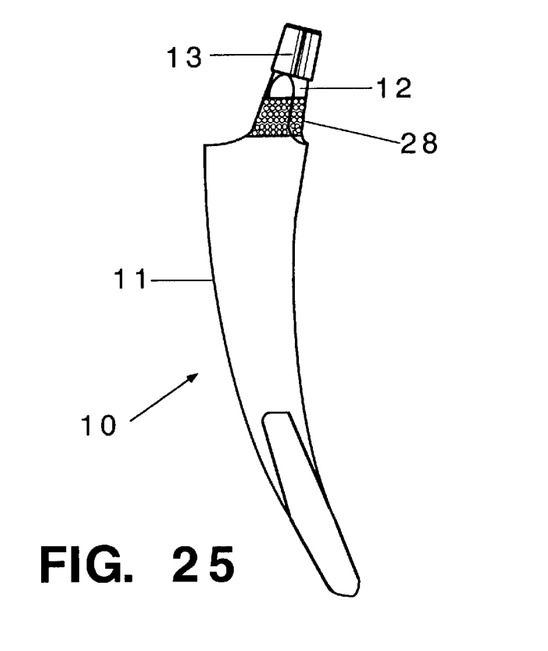
FIG. 25 is a ventral view of the component of FIG. 24, with the dorsal view being a mirror image thereof.
Figure 26:
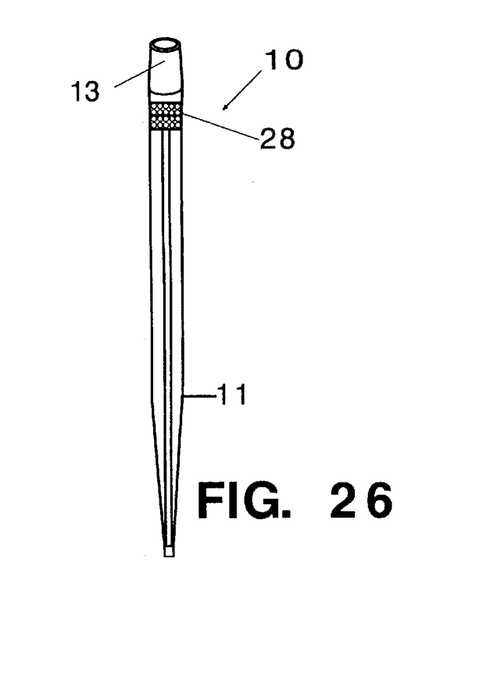
FIG. 26 is a medial view of the component of FIGS. 24 & 25.
Figures 27, 28:
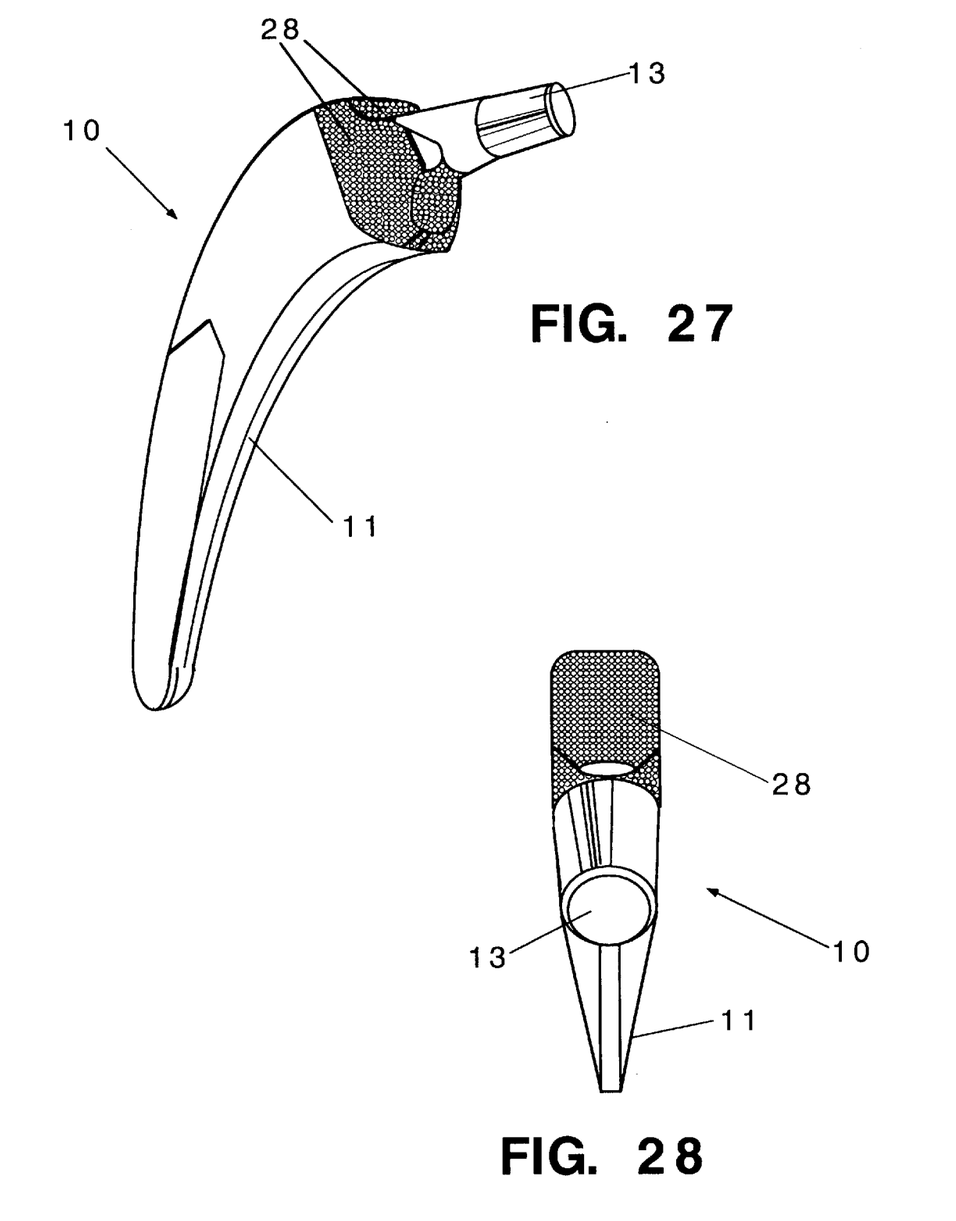
FIG. 27 is a perspective view of the FIGS. 24–26 component.
FIG. 28 is a proximal view of the component of FIGS. 24–27.
Figure 29:
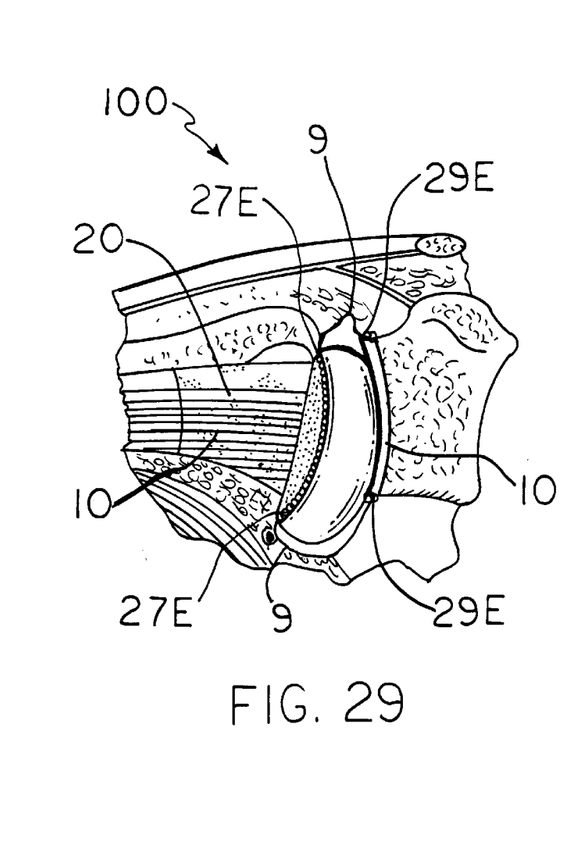
FIG. 29 is a ventral view of another embodiment of the invention, embodied as another enarthrodial type joint, a total shoulder joint replacement implant ensemble.
Figure 30:
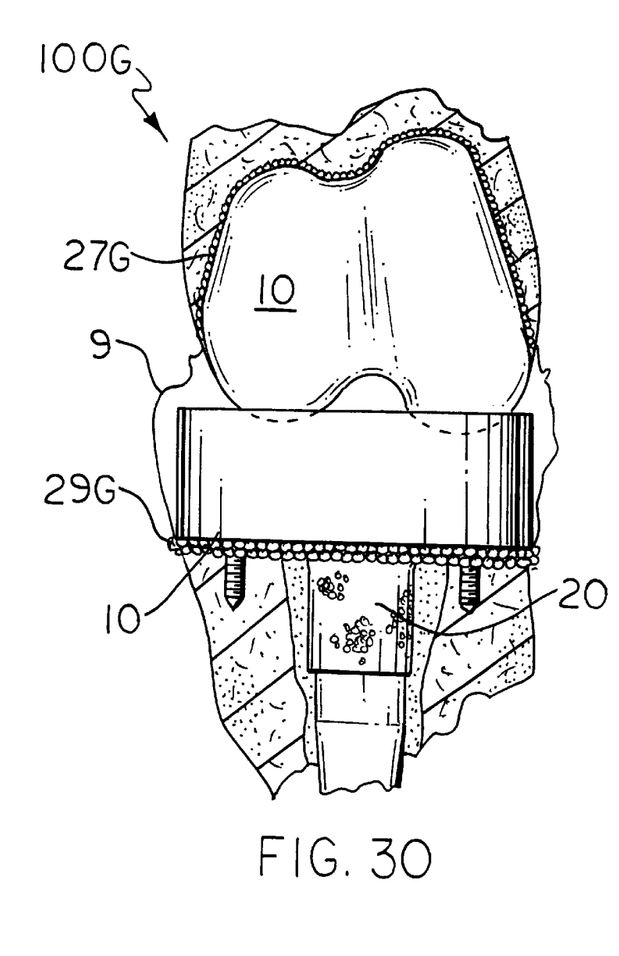
FIG. 30 is a ventral view of another embodiment of the invention, embodied as a ginglymous type joint, a total knee, joint replacement implant ensemble.

In general, with respect to the drawings, prosthetic component 10 (FIGS. 1–8 & 9–28). is depicted as part of a total, conventional hip joint replacement implant ensemble 100 (FIG. 6). The hip prosthesis component 10 can be the stem component of a femoral component (FIGS. 105 & 9–28) or part of an acetabular cup or assembly therefor (FIGS. 7 & 8). Prosthetic components 10 are also depicted as parts of a total shoulder joint replacement implant ensemble 100E (FIG. 29) and a total knee joint replacement implant ensemble 100G (FIG. 30).

More particularly, the component 10 can have metal stem 11, which may be cemented in place by surgical cement 11c, and non-bone-interfacing neck 12 and trunion 13 for receiving metal or ceramic head 14. As an alternative, a one-piece femoral component may be provided in lieu of the femoral component assembly. However, the component 10 for total, conventional hip replacement can optionally but preferably include collar or platform 15 between the stem 11 and the neck 12 and trunion 13. The collar 15 generally includes proximally directed obverse face 16, superficially directed side face 17, and distally directed reverse face 18, which is the bone-interfacing surface of the collar 15. Acetabular cup 19, for example, of UHMWPE, includes a head-mating, articulating surface 19a, and can include metal backing 19b and cup-to-backing sealing cap 19c that is monolithic in structure with the remainder of the cup 19 made of UHMWPE. The backing 19b may be provided with a cup cap receiving hole 19bc and screw holes 19bs (FIG. 8). As an alternative, a one-piece acetabular cup may be provided such as of plastic, for example, UHMWPE. As is well known, the head 14 of the femoral component mates with and articulates with the articulating surface 19a of the cup 19. As an option, the stem 11 and cup 19 having the metal backing 19b may be provided with porous coating 20 for periprosthetic bone ingrowth fixation (FIGS. 1–4, 6 in part, 7, 9, 11–13 & 19–22). Otherwise or in addition, such may be provided with smooth surface irregularities such as grooves in such a form as may be adapted for cement interdigitation fixation (FIGS. 1–4 & 6 in part, 15–18 & 24–28). Fins and/or coxcombs may also be provided (FIGS. 1–18).

Extramedullary, non-bone-interfacing rough surface is provided, which engenders ingrowth of fibrous tissue. For example, non-bone-interfacing metal porous coating can be provided on a portion of the obverse face 16 of the collar or platform 15, forming an obverse face pore coating 26 and/or on a portion or all of the side face 17, forming a side face pore coating 27, which may extend about the entire periphery of thee platform 15 (FIGS. 1–6 & 9–18). Thus, with the femoral hip stem of FIGS. 9 & 10, the top (proximal part) 16 of the platform 15 is porous coated 26 on its raised, central, medial portion from the edge 17 to 0.125 inches (") back; on the lateral portion, porous coating 26 is applied from the edge 17 to a point 0.262" from the end of the side grooves; and porous coating 27 is applied around the outer edge 17 of the platform 15. The porous coatings 26, 27 can blended using a radius. Porous coating 20 further can be applied on intramedullar surfaces for bone fixation such as on the tapered platform continuing down (distally) the stem 11, say, to a point 0.125" below the fin, and the flat two sides of the fin can also have applied the intramedullary porous coating 20. Continuing further, the non-bone-interfacing rough surface can be provided simply on part of a collarless stem which is intended to be an extramedullary, obverse surface such as by metal porous coating 28 (FIGS. 19–28). The non-bone-interfacing rough surface can be provided on a part of a corresponding cup or cup backing such as by extramedullary metal porous coating 29 (FIGS. 6–8)y. Although the rough surface is beneficially a metal porous coat, for example, a cobalt-chromium-molybdenum powder type pore coat applied in accordance with ASTM F 1377-98 to a cobalt-containing alloy component made with ASTM F 75-92, ASTM F 799-95 or ASTM F 1537-94 in mind, the rough surface does not need to be in the form of a porous coat, nor need the metal component and matching metallic rough surface be limited to the use of cobalt-chrome alloys. For example, a porous mesh material may be employed in lieu or in conjunction with a porous metal coating. With plastic components, abrasion of an extramedullary surface such as with the teeth of a saw or rasp may provide a suitable rough surface for ingrowth of fibrous tissue, or loop material may be sewn, melted, or glued in the extramedullary surface to provide the rough surface. In general, the component and the surface roughening may be fabricated from any suitable, biocompatible, high-strength material such as, for example, titanium or titanium alloy. A ceramic may be employed.

One or more components may make up a prosthesis, and assembly and/or implantation of the component(s) 10 can provide the joint implant ensemble 100. Accordingly, for example, the component 10 in the form of the headless stem 11 (FIGS. 1–5 & 9–28); the head-containing femoral component assembly 11, 14 (FIG. 6), the joint ensemble 100 which includes the femoral component assembly 11, 14 and acetabular cup 19 (FIG. 6), and the component 10 in the form of the acetabular cup 19 (FIGS. 6–8) are within the scope of the invention.

With implantation of the component 10 and/or prosthesis 100, for example, into femur 7 and hip 8, the non-bone-interfacing rough surface such as the pore coated surfaces 26, 27, 28 engenders the ingrowth of soft fibrous tissue 9 from the hip bone area such as connective and/or scar tissue. In a relatively short time, it forms, as it were, a reconstituted, capsular containment ("bag") in which wear debris such as UHMWPE wear debris is trapped, and so, those particles are kept from gaining access to supporting bone at the bone-prosthetic interface, with wear debris-induced osteolysis able to be ameliorated or eliminated. From time to time, the contents of the "bag" can be flushed out, for example, by employing needle aspiration.

The principles of the aforementioned illustrative hip embodiment can be more broadly applied to other joints. For example, other enarthrodial joint implants for the body such as those for the shoulder, and ginglymous joint implants such as for the elbow and knee can be provided with a suitable rough, non-bone-interfacing surface into which fibrous tissue can grow and form a similar "bag" for mitigation of wear debris dispersion. To encourage formation of such a reconstituted, capsular "bag," it is advantageous to provide the suitable rough surface on peripheral extramedullary boundaries of the implant component under consideration. For example, in the shoulder ensemble 100E (FIG. 29) the suitable rough surface 27E is on the peripheral, non-bone-interfacing boundary of one component 10 (humeral stem), and the suitable rough surface 29E is on the bit peripheral, non-bone-interfacing boundary of another component 10 (glenoid cup), so as to engender growth of the capsular bag 9; and in the knee ensemble 100G (FIG. 30) the suitable rough surface 27G is on the peripheral, non-bone-interfacing boundary of one component 10 (femoral condyle-containing component), and the suitable rough surface 29G is on the peripheral, non-bone-interfacing boundary of another component 10 (tibial tray support component), so as to engender growth of the capsular bag 9.

CONCLUSION

The present invention is thus provided. Features, parts, subcbmbinations and combinations may be practiced with or without reference to other features, parts, subcombinations or combinations of the invention, and numerous adaptations and modifications can be effected in its spirit, the literal claim scope of which is particularly pointed out as follows:

I claim:

1. A modular prosthetic component comprising an artificial joint implant component including a stem for insertion into a long bone and a platform having peripheral side faces and obverse face, said platform for residing on the bone, on which platform opposite the stem a trunion for receiving a separate, corresponding joint head is positioned, which component has a non-bone-interfacing rough surface suitable for ingrowth of fibrous tissue, wherein said rough surface is provided about surfaces on peripheral boundaries of the component on at least part of the peripheral side faces of the platform.

2. The component of claim 1, which is made of metal.

3. The component of claim 2, wherein said rough surface is a metal porous coating.

4. The component of claim 3, which is part of a total joint replacement implant having a plurality of components.

5. The component of claim 1, which is an enarthrodial joint implant.

6. The component of claim 5, wherein said rough surface is provided on all peripheral side faces of the platform.

7. The component of claim 6, which is a femoral component for a total, conventional hip replacement.

8. The component of claim 7, which includes as the stem an elongate, distally directable stem; as the platform a proximally located platform attached to the stem a neck located in a more proximal direction attached to the platform; at least one of a head, and a trunion for receiving the head, located in an even more proximal direction and attached to the neck.

9. The component of claim 1, wherein said rough surface is provided on a portion of said obverse face.

10. A prosthetic component comprising an artificial joint implant component for a total, conventional hip replacement, having a non-bone-interfacing rough surface suitable for ingrowth of fibrous tissue, wherein said rough surface is provided on the component for implantation into a femur, which implant component in a femoral component and which includes an elongate stem; a proximally located platform attached to the stem; a neck located in a more proximal direction attached to the platform; at least one of a head, and a trunion for receiving a head, located in an even more proximal direction and attached to the neck; and, on at least part of the platform, said rough surface, wherein said component is made of metal, and wherein said rough surface is provided on peripheral side faces and at least a portion of an obverse face of the platform.

11. The component of claim 10, wherein said rough surface is provided by a porous metal coating.

12. The component of claim 11, which is modular and includes the trunion for receiving the head, which is separate from and corresponds to the trunion.

13. The component of claim 12, which includes the head.

14. The component of claim 13, wherein the head is ceramic.

15. A total replacement joint ensemble comprising:
   a first joint implant component with a first articulating surface and further including a platform having peripheral side faces and an obverse face, said platform for residing on the bone, generally on which platform opposite the obverse face the first articulating surface is positioned, and
   a second joint implant component with a corresponding second articulating surface for mating with the first articulating surface of said first component;
wherein said first component has a non-bone-interfacing rough surface suitable for ingrowth of fibrous tissue, wherein said rough surface is provided about faces on peripheral boundaries of the component on at least part of the peripheral side faces of the platform.

16. The ensemble of claim 15, which is a replacement hip joint ensemble.

17. The ensemble of claim 15, wherein said second component has a non-bone-interfacing rough surface suitable for ingrowth of fibrous tissue about surfaces on peripheral boundaries of the component.

18. The ensemble of claim 16, wherein said second component, which is an acetabular cup component, has a non-bone-interfacing rough surface suitable for ingrowth of fibrous tissue about surfaces on peripheral boundaries of the component.

19. The ensemble of claim 15, which is a replacement shoulder joint ensemble or is a replacement ginglymous joint ensemble.

20. The ensemble of claim 15, wherein said rough surface is provided on a portion of the obverse face of the platform of said first joint implant component.

* * * * *